United States Patent [19]
Leong et al.

[11] Patent Number: 5,531,105
[45] Date of Patent: Jul. 2, 1996

[54] METHOD AND SYSTEM FOR DETERMINING ENGINE OIL CONSUMPTION

[75] Inventors: Dick Y. Leong, Bloomfield Hills; Alex D. Colvin, Oak Park; Keith R. Carduner, Dearborn, all of Mich.

[73] Assignee: Ford Motor Company, Dearborn, Mich.

[21] Appl. No.: 422,400

[22] Filed: Apr. 14, 1995

[51] Int. Cl.⁶ .................................................. G01M 15/00
[52] U.S. Cl. .............................................. 73/116; 73/23.31
[58] Field of Search .................................. 73/116, 117.3, 73/118.1, 118.2, 23.31

[56] References Cited

U.S. PATENT DOCUMENTS

| | | | |
|---|---|---|---|
| 4,029,563 | 6/1977 | Binder et al. | 204/1 F |
| 4,277,368 | 7/1981 | Amy et al. | 252/408 |
| 4,321,056 | 3/1982 | Dimitroff | 73/116 |
| 4,391,690 | 7/1983 | Lin et al. | 204/412 |
| 4,499,190 | 2/1985 | Spicer et al. | 436/122 |
| 4,622,105 | 11/1986 | Liu et al. | 204/1 T |
| 5,117,680 | 6/1992 | Colvin | 73/116 |
| 5,129,257 | 7/1992 | Carduner et al. | 73/116 |
| 5,152,963 | 10/1992 | Wreyford | 422/80 |

OTHER PUBLICATIONS

"An Advanced Instrument for the Real Time Measurement of Engine Oil Economy", Alex D. Colvin et al, SAE Technical Bulletin No. 920655, Feb. 24–28, 1992.

Primary Examiner—Richard Chilcot
Assistant Examiner—George M. Dombroske
Attorney, Agent, or Firm—Peter Abolins; Roger L. May

[57] ABSTRACT

A method and system for determining steady state and real time engine oil consumption of an automotive engine which generates exhaust gases containing oil and fuel having a known sulphur content. The system includes an exhaust gas conditioner coupled to the exhaust manifold of the engine for extracting an exhaust gas sample and converting the exhaust sample into a combustion product. The system also includes a high temperature sampler for automatically regulating the amount of the combustion product independent of changes in back pressure of the engine. The system further includes a fluorescent detector for generating a sulphur dioxide content signal having a value corresponding to the sulphur dioxide contained in the regulated combustion product. Finally, the system includes a processor responsive to the value of the sulphur dioxide content signal to determine a steady state and/or a real time oil consumption of the engine based on the value of the sulphur dioxide content signal and the known sulphur content of the oil and fuel.

20 Claims, 1 Drawing Sheet

METHOD AND SYSTEM FOR DETERMINING ENGINE OIL CONSUMPTION

TECHNICAL FIELD

This invention relates to methods and systems for determining engine oil consumption, and more particularly, to methods and systems for automatically determining engine oil consumption under both steady state and transient engine operating conditions.

BACKGROUND ART

It is desirable for engine manufacturers to have a means for determining engine oil consumption quickly, accurately and automatically. Studies have shown that consumers consider the need to add oil to an engine between oil changes is representative of problems with engine design or performance. In addition, high oil consumption has been correlated with premature aging of catalytic converters and exhaust gas oxygen sensors, as well as high levels of hydrocarbons in the exhaust gas.

U.S. Pat. No. 5,129,257 to Carduner et al. discloses a method for determining engine oil consumption on a real-time basis. A control circuit operates to maintain a small, constant concentration of a selected electrolyte constituent reactive with the exhaust constituent sought to be measured. The amount of current necessary to regenerate and maintain the concentration of the selected electrolyte constituent is continuously measured to generate a real-time electrical signal proportional to the mass flow of the exhaust constituent entering the electrochemical cell. If the exhaust contains less than 2500 ppm of nitric oxide (NO), potassium nitrite in the electrolyte will overcome nitrogen dioxide ($NO_2$) gas interference. However, the electrochemical cell is susceptible to $NO_2$ gas interference in an exhaust containing more than 2500 ppm of NO due to the formation of $NO_2$ resulting from a chemical reaction of NO and $O_2$.

Another known method for determining engine oil consumption involves detecting $SO_2$ utilizing ultra violet fluorescence analysis of a conditioned exhaust stream. Such a method is disclosed in U.S. Pat. No. 5,152,963 to Wreyford. A sample is first combusted to provide products of combustion, including $SO_2$ and NO. The sample is then passed through a dryer to eliminate any water condensation. Next, the sample is directed into two different chambers: a reaction chamber for determining the nitrogen content of the sample, and a fluorescent chamber for determining the sulphur content of the sample. This system suffers from the drawback that it requires a permeation dryer which requires routine maintenance and deteriorates gradually without prior notice.

Accordingly, there exists a need for a simplified method and system for accurately and quickly determining engine oil consumption for both steady state engine operation as well as transient modes of engine operation.

DISCLOSURE OF THE INVENTION

It is thus a general object of the present invention to provide a method and system for quickly, accurately and automatically determining engine oil consumption based on a known sulphur content of the oil and the fuel consumed in the engine.

In carrying out the above object and other objects, features and advantages, of the present invention, a method is provided for determining engine oil consumption. The method includes the initial step of extracting a fixed amount of an exhaust gas sample from an engine independent of the exhaust flow through the engine. Next, the exhaust gas sample is converted into a combustion product. The method continues to transfer the combustion product to a fluorescent detector which is designed to measure atmospheric levels of sulphur dioxide ($SO_2$) contained in the combustion product. Finally, the method concludes with the step of automatically determining the oil consumption of the engine based on the sulphur dioxide content of the combustion product and the known sulphur content of the oil and fuel.

Preferably, the method includes doping the exhaust gas sample with oxygen prior to converting the exhaust gas sample into the combustion product so as to eliminate interference from carbon monoxide and hydrocarbon gas. The method also preferably includes doping the combustion product with ozone prior to determining the sulphur dioxide content of the combustion product so as to eliminate the interference from nitric oxide (NO).

In further carrying out the above object and other objects, features and advantages, of the present invention, a system is also provided for carrying out the steps of the above described method.

The system includes an exhaust conditioner coupled to the exhaust manifold of the engine for extracting an exhaust gas sample and burning the exhaust gas sample into a combustion product. The system also includes a high temperature sampler coupled to the exhaust conditioner for automatically regulating the amount of the combustion product independent of changes in back pressure of the engine. Furthermore, the system includes a fluorescent detector having an input coupled to the sampler as a means for receiving the combustion product and generating a sulphur dioxide content signal corresponding to the sulphur dioxide content of the combustion product. Finally, the system includes a processor coupled to the fluorescent detector responsive to the sulphur dioxide content signal to determine a steady state oil consumption and/or a real time oil consumption of the engine based on the value of the sulphur dioxide content signal and the known sulphur content of the oil and the fuel.

The high temperature sampler preferably comprises a heated sample flow line coupled to the exhaust conditioner for removing the combustion product from the exhaust conditioner, a mass flow controller coupled to the heated sample flow line for controlling a total flow rate of the combustion product, and a high temperature control valve disposed between the heated sample flow line and the mass flow controller for controlling the flow of the combustion product to the mass flow controller.

Preferably, the system includes a first doping means coupled to the exhaust conditioner for doping the exhaust gas sample with oxygen so as to eliminate interference from carbon monoxide and hydrocarbon gas. The system also preferably includes a second doping means coupled to the high temperature sampler for doping the combustion product with ozone so as to eliminate interference from nitric oxide.

The above objects, features and advantages of the present invention, as well as others, are readily apparent from the following detailed description of the best mode for carrying out the invention when taken in connection with the accompanying drawing.

BEST MODE FOR CARRYING OUT THE INVENTION

Figure 1:
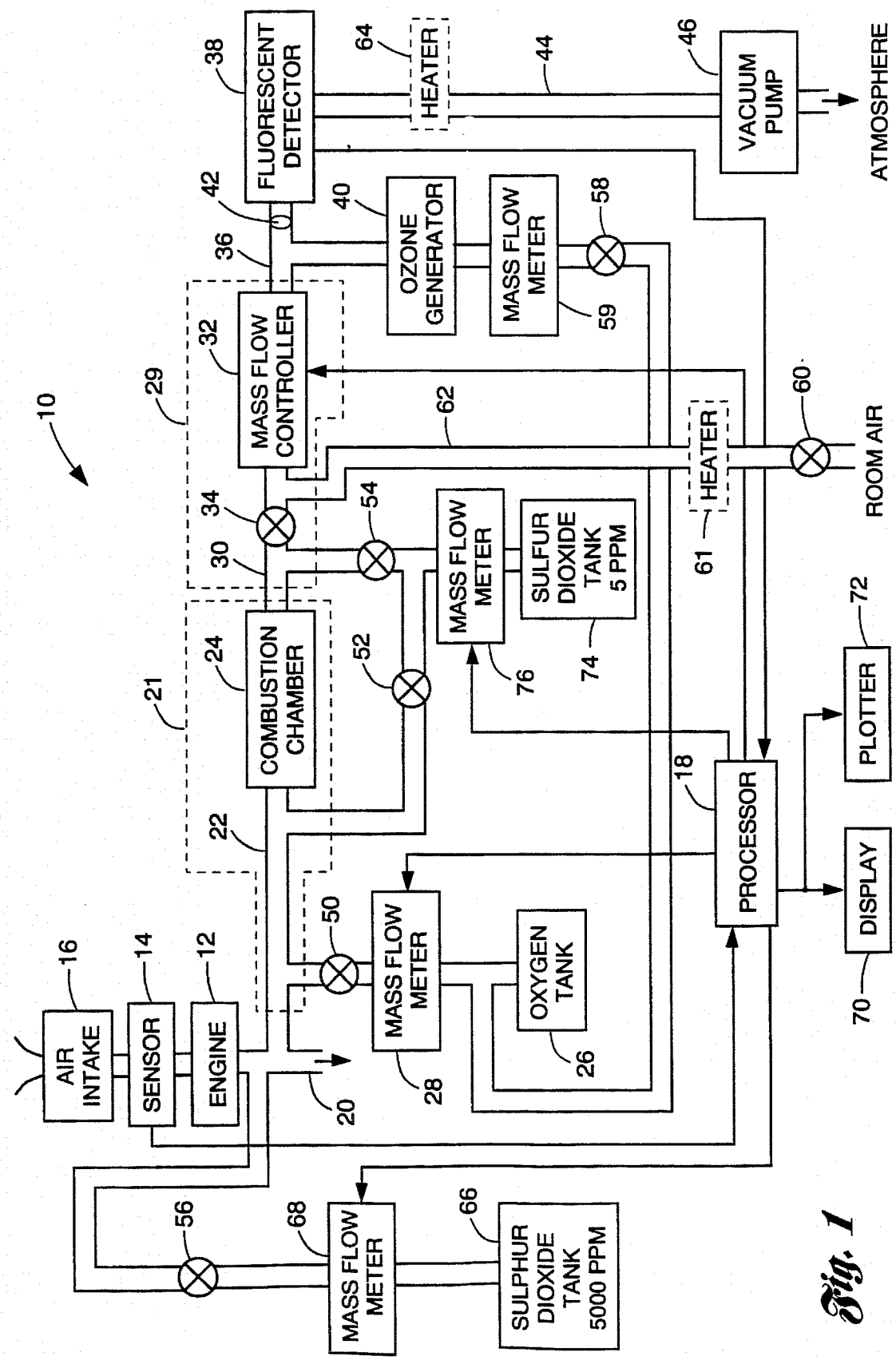
FIG. 1 is a block diagram of a system for determining the oil consumption of an engine according to the present invention.

Referring to FIG. 1, there is shown a block diagram of a system for determining oil consumption of an engine, denoted generally by reference numeral 10. In order to determine the quantity of oil consumed by an engine, the system 10 senses the sulphur found naturally in all petroleum-based fuels and lubricants. Assuming there are no oil leaks in the engine, all oil consumed by the engine proceeds into the exhaust gases where approximately 98% of the sulphur from the oil and fuel reacts to form sulphur dioxide ($SO_2$).

The system 10 includes an engine 12 having a mass air flow sensor 14 for determining the quantity of air flowing to the engine 12 through an air intake 16. The mass air flow sensor 14 may comprise a conventional mass air flow sensor associated with an electronic fuel control system of the engine 12. Alternatively, the sensor 14 could comprise a laminar flow element or other type of sensor known to those skilled in the art. The mass air flow sensor 14 generates a mass air flow signal corresponding to the mass air flow to the engine 12 and transmits this information to a processor 18.

As the engine 12 burns the fuel mixture, exhaust gases are generated and emitted from the engine 12 into an exhaust manifold 20. A sample of the exhaust gases having partially burned oil and residual fuel is extracted and converted into carbon dioxide, sulphur dioxide and water vapor utilizing an exhaust conditioner means 21 comprising a sample line 22 and a combustion chamber 24. The conversion of the exhaust sample eliminates any interference from carbon monoxide and hydrocarbon gases present in the exhaust gases.

A fixed sample of the exhaust gases in an amount independent of the engine air flow through the engine is drawn through the sample line 22. Before entering the combustion chamber 24, the exhaust sample is doped with additional oxygen to promote the complete combustion of reactive material in the exhaust gas sample. The oxygen is provided from an oxygen tank 26 which passes through the oxygen flow meter 28 in response to commands from the processor 18.

The doped exhaust gas sample is then transferred to the combustion chamber 24 which completes the oxidation of any unburned hydrocarbons, oxidizes the sulphur to form $SO_2$, and converts some of the oxides of nitrogen to $NO_2$. The combustion chamber 24 is held at a temperature of about 1000° Centigrade. The combustion chamber 24 is also, preferably, constructed out of an alloy, such as RA330, manufactured by Rolled Alloys, Inc.

The converted exhaust gas sample passes from the exhaust conditioner to a high temperature sampler 29 comprising a heated sample flow line 30, a mass flow controller 32 and a high temperature control valve 34. The mass flow controller 32 automatically regulates the flow of the exhaust gas sample so that the system 10 is insensitive to engine back pressure changes.

The converted exhaust gas sample passes through the heated sample flow line 30 which prevents the formation of water condensation. Thus, the need for an additional dryer is eliminated. The heated gas sample flow line 30 is preferably held at a temperature of approximately 350° Centigrade.

The high temperature control valve 34 maintains the gas temperature above a temperature of 80° Centigrade into the mass flow controller 32.

The mass flow controller 32 controls the total flow rate of the converted exhaust gas sample. The mass flow controller 32 also restricts the flow, lowering the gas pressure to approximately 10" Hg absolute, lowering the dew point. With a lower dew point, the converted exhaust gas sample can be maintained at a lower temperature without water condensation.

The converted exhaust sample passes from the high temperature sampler 29 via tube 36 connected to the inlet of a fluorescent detector 38 for determining the sulphur concentration of the converted exhaust gas sample. A pulsed fluorescent detector such as a Model 43B, manufactured by Thermo Environmental Instruments, Inc. may be utilized. Prior to entering the fluorescent detector 38, the converted exhaust gas sample is doped with ozone which reacts with any residual NO to form $NO_2$, thus, reducing gas interference. The ozone is provided from an ozone generator 40. The elevated temperature of the exhaust sample and the addition of oxygen and ozone to the sample allows the elimination of a permeation dryer which is used to reduce water content in the sample. The absorption of $SO_2$ by the condensed water would cause an error in the oil consumption determination. The use of a permeation dryer to remove the water vapor requires routine maintenance and its performance deteriorates gradually without warning.

Immediately before entering the fluorescent detector 38, the converted and doped exhaust gas sample flows through a stainless steel filter 42, preferably a #1 Hoke metallic filter, as manufactured by Hoke Inc. to ensure that exhaust particles do not enter the fluorescent detector 38. The stainless steel filter 42 eliminates routine maintenance required by a conventional glass or Epoxy coalescing filter.

Once inside the fluorescent detector 38, the exhaust sample is radiated with 10 Hz bursts of ultraviolet light. The light passes through a bandpass filter (not shown), and a photomultiplier tube (not shown) measure the light intensity at the characteristic wavelengths of $SO_2$. Preferably, the fluorescent detector 38 has a response time of less than four seconds without any interference from NO up to a concentration of 4000 parts per million (ppm) at a flow rate of 1000 cc/min. The fluorescent detector 38 transmits a 0–10 volt signal to the processor 18 proportional to the sulphur dioxide content in the fluorescent detector 38.

After flowing through the fluorescent detector 38, the sample flows through a stainless steel outlet tube 44 maintained at a temperature of approximately 300 centigrade by a heater 64. The heated outlet tube 44 ensures the ozone is neutralized before it is released into the atmosphere. Finally, the sample flows through the outlet tube 44 to a vacuum pump 46 before being discharged to the atmosphere.

Three modes of operation are required in order to determine oil consumption. During the first mode of operation, the system 10 measures the $SO_2$ concentration in the exhaust gas sample due only to burned oil and fuel. First, valves 34, 52, 54 and 56 are closed, and valve 60 is opened. The system 10 then draws a room air sample, e.g. approximately 2000 cc/min, from a filtered port through valve 60 and through a heated tube 62 heated to approximately 300°–350° F. The heated tube 62 is heated by a heater 61 as a precaution to eliminate ozone flow out of the analyzer system 10 in the case of a vacuum pump failure. The sample then flows through the mass flow controller 32 and into the fluorescent detector 38. The heater 64 raises the sample temperature to approximately 350° Centigrade to destroy all the ozone before the vacuum pump 46 passes the sample to the atmosphere.

The signal level output generated by the fluorescent detector 38 is conveyed to the processor 18 and is recorded by the processor as a "Baseline" value. This corresponds to a concentration of $SO_2$ in the ambient room air.

The second mode of operation is conducted with the engine operating. This second mode begins with the opening of valve 34 and the closing of valve 60. The processor 18 then combines $O_2$ gas passed through valve 50 to the exhaust gas sample in sample line 22 to begin the oxidation of any unburned hydrocarbons. The sample and the $O_2$ flow into the combustion chamber 24 which completes the oxidation of any unburned hydrocarbons, oxidizes the sulphur to form $SO_2$, and converts some of the oxides of nitrogen to $NO_2$.

The heated sample flow line 30 maintains the converted exhaust gas sample at a temperature of 350° Centigrade as the exhaust gas sample flows from the combustion chamber 24 to prevent water condensation and eliminate carbon build up in the case of a combustion chamber 24 failure. From the heated sample flow line 30, the mixed exhaust gas sample and $O_2$ flow through the high temperature control valve 34 and the mass flow controller 32 into the fluorescent detector 38. The exhaust gas sample is then mixed with approximately 1000 cc/min of 5,000 ppm ozone ($O_3$) passed from the ozone generator 40. The $O_3$ reacts with any residual NO in the exhaust gas sample to form $NO_2$.

The signal level output of the fluorescent detector 38 is conveyed to the processor 18 where it is recorded by the processor 18 as an "Engine" value.

The third mode of operation is identical to the second mode of operation except the valve 56 is opened to permit the addition of $SO_2$ into the exhaust gas sample. The addition of a known quantity of $SO_2$ allows engine oil consumption to be determined independent of the exhaust flow through the engine. The processor 18 injects approximately 1000 cc/min of $SO_2$ gas from a first $SO_2$ tank 66 into the engine exhaust pipe 20 of the engine 12. The $SO_2$ gas flow is controlled by valve 56 and is measured by mass flow meter 68. The signal level output of the fluorescent detector 38 is conveyed to the processor 18 where it is recorded as an "EngPlusSO$_2$" value.

Assuming the oil consumption rate during the "EngPlusSO$_2$" mode repeats during the "Engine" mode, the signal due to the injected $SO_2$ gas can be used as a calibration constant to convert the signal due to engine exhaust ("Engine"—"Baseline") to a measure of $SO_2$ concentration and then to total exhaust stream content, expressed in grams per hour. The oil consumption can then be determined based on the following:

Sulphur from SO2 = (1)

$$\frac{\text{SO2InTank PPM} * \text{SO2Flow cc/min} * 32 \text{ g/mol} * 60 \text{ min/hr}}{22414 \text{ cc/mole} * 10^6 \text{ PPM}},$$

where SO2InTank PPM represents the concentration of $SO_2$ in the tank 66, and SO2Flow represents the $SO_2$ flow rate.

*Sulphur from SO2*=$8.566 \times 10^{-8}$**SO2InTank*SO2Flow g/hr* (2)

*Sulphur from Oil=OilConsUncorgph*SInOil*/100%, (3)

where OilConsUncorgph represents the uncorrected oil consumption in g/hr, and SInOil % represents the percentage of sulphur contained in the oil.

Sulphur from Oil = 0.0100 * OilConsUncorgph * SInOil g/hr (4)

$$\frac{\text{Sulphur from Oil}}{\text{Sulphur from SO2}} = \frac{\text{Val[Engine]} - \text{Val[Baseline]}}{\text{Val[EngPlusSO2]} - \text{Val[Engine]}} \quad (5)$$

OilConsUncorgph = 100 * Sulphur from Oil/SInOil (6)

OilConsUncorgph = (7)

$$\frac{100 * (\text{Val[Engine]} - \text{Val[Baseline]})}{(\text{Val[EngPlusSO2]} - \text{Val[Engine]}) * \text{SInOil}} *$$

$$8.566 \times 10^{-8} * \text{SO2InTank} * \text{SO2Flow g/hr} = 8.566 \times 10^{-6} *$$

$$\frac{(\text{Val[Engine]} - \text{Val[Baseline]}) * \text{SO2Flow} * \text{SO2InTank}}{\text{SInOil} * (\text{Val[EngPlusSO2]} - \text{Val[Engine]})} \text{ g/hr}$$

The system 10 applies a correction factor, FuelCorrectiongph, to the oil consumption rate based on the measured fuel flow rate to eliminate the signal due to fuel:

FuelCorrectiongph = (8)

$$\frac{\text{SInFuel kg S/kg fuel PPM} * \text{FuelFlow kg/hr}}{\text{SInOil kg S/kg oil \%}} *$$

$$\frac{1000 \text{ g}}{1 \text{ kg}} * \frac{1\%}{10000 \text{ PPM}},$$

where FuelFlow represents fuel flow in kilogram/hour $$\text{FuelCorrectiongph} = \frac{\text{SInFuel} * \text{FuelFlow}}{\text{SInOil} * 10} \text{ g oil/hr} \times \text{oil}, \quad (9)$$

where SinFuel represents the amount of sulphur contained in the fuel.

*OilConsgph=OilConsUncorrgph−FuelCorrectiongph,* (10)

where OilConsgph represents the oil consumption of the engine in grams per hour.

The system 10 determines the oil consumption rate of an engine over a predetermined time interval, $\Delta t$. During the predetermined time interval, the oil consumption rate is also calculated at predetermined intermediate time intervals within the predetermined time interval to obtain the transient, or real time, rate of oil consumption. The steady state oil consumption rate is determined by averaging the transient rates over the predetermined time interval.

The results of the engine oil consumption may be read on either a display 70 or a plotter 72.

The system 10 is calibrated utilizing $SO_2$ gas from a second $SO_2$ tank 74. The second $SO_2$ tank contains a concentration of 5 ppm $SO_2$ and is measured by mass flow meter 76. The calibration mode of operation is identical to the second and third mode of operation except valves 54 and 56 are closed and valve 52 is opened. The processor 18 directs approximately 0–500 cc/min of $SO_2$ gas flow through the mass flow meter 76 and the valve 52.

The processor 18 also directs enough $O_2$ gas from the $O_2$ tank 26 through mass flow meter 28 and valve 50 so that the sum of the $O_2$ and $SO_2$ gas flow rates are greater than the total mass flow rate. As a result, a portion of the $O_2$ gas is forced into the exhaust stream to eliminate signal contamination by engine exhaust.

The $O_2$ and $SO_2$ gas is received by the fluorescent detector 38 which measures the $SO_2$ concentration in the sample flow to determine the system calibration.

While the best modes for carrying out the invention have been described in detail, those familiar with the art to which this invention relates will recognize various alternative designs and embodiments for practicing the invention as defined by the following claims.

What is claimed is:

1. For use with an automotive engine having an exhaust manifold and containing oil and fuel with a known sulphur content, a method for determining oil consumption of the engine, the method comprising:

extracting an exhaust gas sample from the engine independent of air flow through the engine;

converting the exhaust gas sample into a combustion product at an elevated temperature;

transferring said combustion product to a fluorescent detector at a temperature and pressure sufficient to prevent the formation of water condensation and at a flow rate sufficient to overcome changes in back pressure of the engine, the pressure being less than atmospheric pressure;

determining a sulphur dioxide content of the combustion product using the fluorescent detector; and automatically determining the oil consumption of the engine in real time based on the sulphur dioxide content of the combustion product and the known sulphur content of the oil and the fuel.

2. The method as recited in claim 1 wherein said step of converting includes the step of doping the exhaust gas sample with a first substance.

3. The method as recited in claim 2 wherein the first substance is oxygen.

4. The method as recited in claim 1 wherein said step of determining a sulphur dioxide content further comprises the step of doping the combustion product with a second substance.

5. The method as recited in claim 4 wherein the second substance is ozone.

6. The method as recited in claim 1 wherein the step of automatically determining the oil consumption of the engine includes determining a steady state oil consumption.

7. The method as recited in claim 1 wherein the step of automatically determining the oil consumption of the engine includes determining a transient oil consumption.

8. For use with an automotive engine having an exhaust manifold and containing oil and fuel with a known sulphur content, a system for determining steady-state and real-time oil consumption of the engine, the system comprising:

an exhaust conditioner coupled to exhaust manifold of the engine for obtaining an exhaust gas sample independent of air flow through the engine and for burning the exhaust sample at an elevated temperature to form a combustion product;

a high temperature sampler coupled to the exhaust conditioner for automatically controlling the temperature and pressure of the combustion product to prevent the formation of water condensation and for regulating the amount of the combustion product independent of changes in back pressure of the engine, the pressure being less than atmospheric pressure;

a fluorescent detector having an input coupled to the sampler, the fluorescent detector receiving the combustion product and generating a sulphur dioxide content signal corresponding to the sulphur dioxide content of the combustion product; and a processor coupled to the fluorescent detector responsive to the sulphur dioxide signal to determine an oil consumption of the engine in real time based on the sulphur dioxide content signal and the known sulphur content of the oil and fuel.

9. The system as recited in claim 8 wherein the exhaust conditioner comprises:

a sample inlet means for extracting an exhaust gas sample; and a high temperature combustion chamber coupled to the sample inlet means for burning the exhaust sample at the elevated temperature to form the combustion product.

10. The system as recited in claim 8 wherein the exhaust conditioner further includes:

a first doping means coupled to the exhaust conditioner for doping the extracted exhaust gas sample with a first substance selected to eliminate interference from carbon monoxide and hydrocarbon gas.

11. The system as recited in claim 10 wherein the first substance is oxygen.

12. The system as recited in claim 8 wherein the combustion means is constructed utilizing an Incoloy material.

13. The system as recited in claim 8 wherein the high temperature sampling means comprises:

a mass flow controller for controlling a total flow rate of the combustion product;

a heated sample flow line for coupling the exhaust conditioner to the mass flow controller; and a high temperature control valve disposed between the heated sample flow line and the mass flow controller for controlling the flow of the combustion product to the mass flow controller.

14. The system as recited in claim 8 wherein the high temperature sampler further comprises:

a second doping means coupled to the high temperature sampling means for doping the combustion product with a second substance so as to eliminate interference with nitric oxide.

15. The system as recited in claim 14 wherein the second substance is ozone.

16. The system as recited in claim 8 wherein the fluorescent detector is an ultraviolet detector.

17. The system as recited in claim 16 wherein the fluorescent detector has a response time of less than four seconds.

18. The system as recited in claim 8 further comprising a vacuum pump coupled to the output of the fluorescent detector for removing the combustion product from the fluorescent detector.

19. The system as recited in claim 8 further comprising a metallic filter disposed between the high temperature sampling means and the input of the fluorescent detector for filtering particles from the combustion product.

20. The system as recited in claim 8 further comprising a heater coupled to the output of the fluorescent detector for removing ozone from the combustion product.

* * * * *